United States Patent [19]
Shirahata et al.

[11] 4,218,562
[45] Aug. 19, 1980

[54] ANTIBIOTIC DERIVATIVES OF XK-62-2

[75] Inventors: Kunikatsu Shirahata, Columbus, Ohio; Shinji Tomioka, Machida, Japan; Takashi Nara, Tokyo, Japan; Hideo Matsushima, Kawasaki, Japan; Isao Matsubara, Machida, Japan

[73] Assignee: Abbott Laboratories, North Chicago, Ill.

[21] Appl. No.: 886,803

[22] Filed: Mar. 15, 1978

Related U.S. Application Data

[60] Division of Ser. No. 692,333, Jun. 3, 1976, Pat. No. 4,109,077, which is a continuation of Ser. No. 531,768, Dec. 11, 1974, abandoned.

[51] Int. Cl.² ........................ A61K 31/71; C07H 15/22
[52] U.S. Cl. ..................................... 536/17 R; 536/18; 424/180
[58] Field of Search ..................................... 536/17, 10

[56] References Cited
U.S. PATENT DOCUMENTS

| 3,780,018 | 12/1973 | Konishi et al. | 536/17 |
| 3,796,698 | 3/1974 | Naito et al. | 536/17 |
| 3,796,699 | 3/1974 | Naito et al. | 536/17 |
| 4,055,715 | 10/1977 | Tomioka et al. | 536/17 |
| 4,076,931 | 2/1978 | Tomioka et al. | 536/17 |
| 4,109,077 | 8/1978 | Shirahata et al. | 536/17 |

Primary Examiner—Johnnie R. Brown
Attorney, Agent, or Firm—Fitzparick, Cella, Harper & Scinto

[57] ABSTRACT

Derivatives of the antibiotic XK-62-2 are prepared by chemically modifying the antibiotic XK-62-2. An example of one such derivative is 1-N-[L-(-)-α-hydroxy-γ-aminobutyryl]XK-62-2.

5 Claims, 8 Drawing Figures

ANTIBIOTIC DERIVATIVES OF XK-62-2

This is a division of application Ser. No. 692,333 filed June 3, 1976, now Pat. No. 4,109,077 which is a continuation of application Ser. No. 531,768, filed Dec. 11, 1974 now abandoned.

BACKGROUND OF THE INVENTION

The present invention relates broadly to semi-synthetic derivatives of the antibiotic XK-62-2 and the production thereof. The antibiotic XK-62-2 and fermentation production thereof are described in U.S. patent application Ser. No. 364,058, filed May 25, 1973.

As is disclosed in the aforementioned U.S. application the antibiotic XK-62-2 is produced readily by culturing actinomycetes such as *Micromonospora sagamiensis*, *Micromonospora ochinospora* and *Micromonospora purpurea* by methods usually employed in the culturing of actinomycetes. More specifically, strains of the above-mentioned microorganisms are inoculated into a liquid medium containing a carbon source which the microorganism can utilize such as sugars, hydrocarbons, alcohols, organic acids, etc.; inorganic or organic nitrogen sources and inorganic salts and growth promoting factors and are cultured at 25°–40° C. for 2 to 12 days. Isolation and purification of XK-62-2 is carried out by a proper combination of adsorption and desorption from ion exchange resins and active carbon and column chromatography using cellulose, Sephadex, alumina and silica gel. In this manner, XK-62-2 can be obtained in the form of the sulfate or in the free form.

XK-62-2 is a basic substance and is obtained as a white powder. XK-62-2 has a molecular formula $C_{20}H_{41}N_5O_7$, and a molecular weight of 463. The substance is well soluble in water and methanol, slightly soluble in ethanol and acetone and insoluble in chloroform, benzene, ethyl acetate and n-hexane.

SUMMARY OF THE INVENTION

In accordance with the present novel antibacterial compounds are produced by chemically modifying the antibiotic XK-62-2 having the following structural formula:

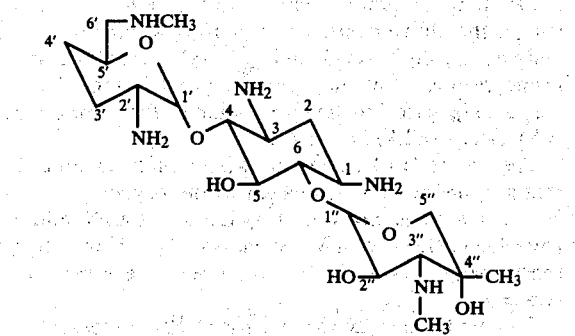

The derivatives of XK-62-2 of the present invention have a strong antibacterial activity against a variety of Gram-positive and Gram-negative bacteria and particularly have a remarkably strong antibacterial activity against those bacteria that are resistant to the known aminoglycoside antibiotics. Accordingly, the antibiotics of the invention are useful to clean and sterilize laboratory glassware and surgical instruments, and may also be used in combination with various soaps for sanitation purposes and in cleaning and sanitizing hospital rooms and areas used for the preparation of food. Further, the derivatives are expected to be effective for the treatment of various infections such as urinary infections and respiratory infections induced by various phlogogenous bacteria.

More specifically, new, semi-synthetic derivatives of XK-62-2 or their pharmaceutically acceptable, non-toxic acid addition salts are prepared by introducing one [in the case of the following (1) and (2) ] or two [in the case of (3) and (4) ] of acyl groups, i.e., α-hydroxy-γaminobutyryl groups to, among the three free amino groups possessed by XK-62-2,: (1) the amino group bonded to the carbon atom at the 2'- position; (2) the amino group bonded to the carbon atom at the 1-position; (3) the amino groups bonded to the carbon atoms at the 2'- and 1-positions, respectively; and (4) the amino groups bonded to the carbon atoms at the 2'- and 3-positions, respectively. That is, the new derivatives of XK-62-2 include:

(1) Compound (I) wherein one of the hydrogen atoms of the amino group bonded to the carbon atom at the 2'-position of XK-62-2 is substituted by

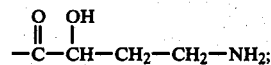

(2) Compound (II) wherein one of the hydrogen atoms of the amino group bonded to the carbon atom at the 1-position of XK-62-2 is substituted by

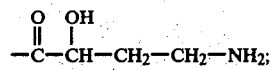

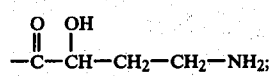

(3) Compound (III) wherein one of the hydrogen atoms of the amino group bonded to the carbon atom at the 2'-position and one of those of the amino group bonded to the carbon atom at the 1-position of XK-62-2 are substituted by

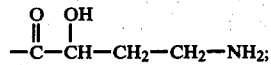

and (4) Compound (IV) wherein one of the hydrogen atoms of the amino group bonded to the carbon atom at the 2'-position and one of those of the amino group bonded to the carbon atom at the 3-position of XK-62-2 are substituted by

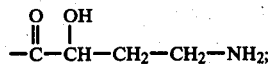

DESCRIPTION OF THE INVENTION

Figure 1:
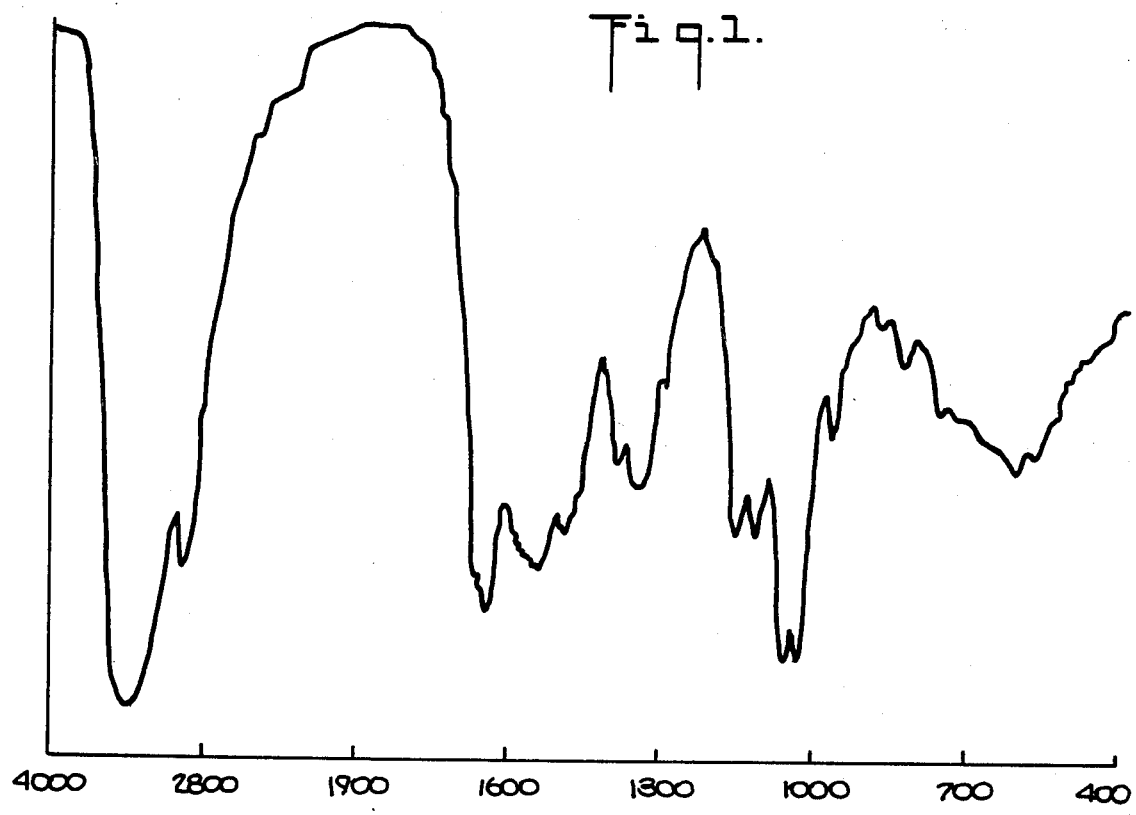
FIG. 1 illustrates the infrared absorption spectrum of 2'-N[L-(—)-α-hydroxy-γ-aminobutyryl] XK-62-2 (compound I)

In accordance with the present invention, the free amino groups of XK-62-2 are acylated with an acylating agent represented by the formula:

$$Y_1\!\!\diagdown\!\!N\text{—}CH_2\text{—}CH_2\text{—}\underset{\underset{OH}{|}}{CH}\text{—}\underset{\underset{}{\overset{O}{\|}}}{C}\text{—}Z$$
$$Y_2\!\!\diagup$$

[wherein $Y_1$ is H and $Y_2$ is:

$R_1,R_2$-substituted benzyl-O-C(=O)—, $CH_3$-C(CH$_3$)(CH$_2$phenyl)-O-C(=O)—, $CH_3$-O-C(=O)—, $C_2H_5$-O-C(=O)—, (phenyl)$_2$C(H)-C(=O)—, $R_3$-CH$_2$-C(=O)—, or 2-nitrophenyl-S—

(wherein $R_1$ and $R_2$ may be the same or different and are H, OH, $NO_2$, Cl, Br, I, alkyl groups having 1 to 5 carbon atoms or alkoxy groups having 1 to 5 carbon atoms and $R_3$ is H, Cl, Br or I); or $Y_1$ and $Y_2$ form a phthaloyl group; and Z is:

—O—N(succinimidyl), —O-phenyl-NO$_2$, —O-phenyl(NO$_2$)$_2$, —O-benzotriazolyl, —N(imidazolyl), Cl, Br, I or OH] (such acylating agents can be derived from α-hydroxy-δ-aminobutyric acid) or a compound functionally equivalent to said acylating agent, to prepare:

(1) Compound (IA) wherein one of the hydrogen atoms of the amino group bonded to the carbon atom at the 2'-position of XK-62-2 is substituted by $$-\underset{\underset{}{\overset{O}{\|}}}{C}\text{—}\underset{\underset{OH}{|}}{CH}\text{—}CH_2\text{—}CH_2\text{—}N\diagdown_{Y_2}^{Y_1};$$

(2) Compound (IIA) wherein one of the hydrogen atoms of the amino group bonded to the carbon atom at the 1-position of XK-62-2 is substituted by $$-\underset{\underset{}{\overset{O}{\|}}}{C}\text{—}\underset{\underset{OH}{|}}{CH}\text{—}CH_2\text{—}CH_2\text{—}N\diagdown_{Y_2}^{Y_1};$$

(3) Compound (IIIA) wherein one of the hydrogen atoms of the amino group bonded to the carbon atom at the 2'-position and one of those of the amino group bonded to the carbon atom at the 1-position of XK-62-2 are substituted by $$-\underset{\underset{}{\overset{O}{\|}}}{C}\text{—}\underset{\underset{OH}{|}}{CH}\text{—}CH_2\text{—}CH_2\text{—}N\diagdown_{Y_2}^{Y_1};$$

and (4) Compound (IVA) wherein one of the hydrogen atoms of the amino group bonded to the carbon atom at the 2'-position and one of those of the amino group bonded to the carbon atom at the 3-position of XK-62-2 are substituted by $$-\underset{\underset{}{\overset{O}{\|}}}{C}\text{—}\underset{\underset{OH}{|}}{CH}\text{—}CH_2\text{—}CH_2\text{—}N\diagdown_{Y_2}^{Y_1};$$

(wherein $Y_1$ and $Y_2$ have the same significance as defined above).

The above-mentioned acylating agents are compounds which are derived from α-hydroxy-δ-aminobutyric acid. It will be apparent to those skilled in the art that compounds which are functionally equivalent to the above-mentioned acylating agent for introducing an α-hydroxy-δ-amibobutyryl group to a free amino group, containing various groups other than ε may also be used for the preparation of the compounds (IA), (IIA), (IIIA) and (IVA).

The methods of acylation, where such compounds that are functionally equivalent to the acylating agents are used, are described in M. Bodansky et al: Synthesis page 453 (1972) and in M. Bodansky et al: Peptide Synthesis, pages 75–135 (1966) (John Wiley & Sons, Inc., U.S.A.).

The acylation reaction is carried out preferably by using an acylating agent of the formula:

$$Y_1\!\!\diagdown\!\!N\text{—}CH_2\text{—}CH_2\text{—}\underset{\underset{OH}{|}}{CH}\text{—}\underset{\underset{}{\overset{O}{\|}}}{C}\text{—}O\text{—}N(succinimidyl)$$
$$Y_2\!\!\diagup$$

(wherein $Y_1$ and $Y_2$ have the same significance as defined above). In this case, a compound of the formula:

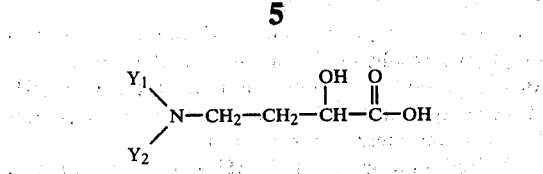

(wherein $Y_1$ and $Y_2$ have the same significance as defined above) may be preliminarily reacted with N-hydroxysuccinimide in the presence of dicyclohexylcarbodiimide to prepare a compound of the formula:

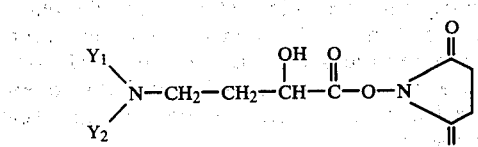

and the resulting compound may be isolated and reacted with XK-62-2.

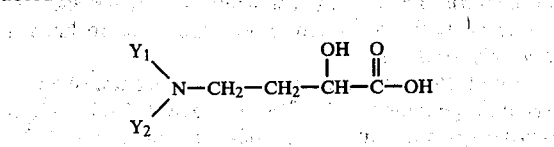

(wherein $Y_1$ and $Y_2$ have the same significance as defined above). N-hydroxysuccinimide and dicyclohexylcarbodiimide are reacted and the resulting reaction mixture is reacted with XK-62-2.

In another embodiment, the acylation reaction may be carried out by adding dicyclohexylcarbodiimide to a mixture of XK-62-2 and a compound of the formula:

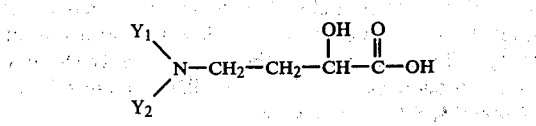

It is to be understood that the aforementioned reactions are applicable where the acylation reaction of XK-62-2 is carried out by any other method and a suitable manner may be selected depending upon the specific acylating agent employed.

Usually, 0.4–2.5 mols, preferably, 0.7–1.5 mols of the acylating agent is used per one mol of XK-62-2. Reaction is carried out at −50° C. to 50° C., preferably −20° C. to 20° C. for 15 minutes to 24 hours, preferably 5 to 15 hours.

Suitable solvents for reaction may be selected from any one or a mixture of two or more of tetrahydrofuran, dimethylacetamide, dimethylformamide, lower alcohols, dioxane, ethylene glycol dimethyl ether, pyridine and water. Preferably, a mixture of ethyl alcohol and water (2:1) is used.

Intermediate compounds IA, IIA, IIIA and IVA prepared in the above manner may be isolated and purified, respectively, for use in the second reaction. However, it is preferable that the reaction mixture is used as it is, without isolation and purifying the acylated compounds. Following the subsequent reaction, compounds I, II, III and IV prepared from the mixture of intermediate compounds are isolated and purified. The latter method is advantageous in simplifying the procedure and enhancing the yield of recovery.

If necessary, compounds IA, IIA, IIIA and IVA may be readily isolated and purified by any of the known methods, for example, column chromatography using an adsorbent such as ion exchange resins, silica gel, alumina, cellulose, Sephadex, etc., and thin layer chromatography using silica gel, alumina, cellulose, etc., as may be easily understood by those skilled in the art.

Compounds IA, IIA, IIIA and IVA (either isolated or in mixture) are then reacted to eliminate the protecting groups $Y_1$ and $Y_2$ in a known manner to prepare: (1) Compound (I) wherein one of the hydrogen atoms of the amino group bonded to the carbon atom at the 2'-position of XK-62-2 is substituted by

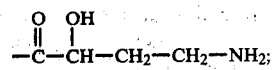

(2) Compound (II) wherein one of the hydrogen atoms of the amino group bonded to the carbon atom at the 1-position of XK-62-2 is substituted by

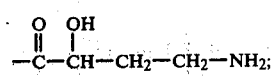

(3) Compound (III) wherein one of the hydrogen atoms of the amino group bonded to the carbon atom at the 2'-position and one of those of the amino group bonded to the carbon atom at the 1-position of XK-62-2 are substituted by

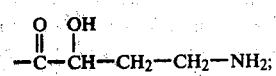

and (4) Compound (IV) wherein one of the hydrogen atoms of the amino group bonded to the carbon atom at the 2'-position and one of those of the amino group bonded to the carbon atom at the 3-position of XK-62-2 are substituted by

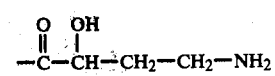

Elimination of the protecting groups may be carried out in a known manner. For example, where the protecting groups form a phthaloyl group, elimination is accomplished with hydrazine; where the protecting group is a carbomethoxy group or carboethoxy group, elimination is accomplished with barium hydroxide; where the protecting group is a tertiary butoxycarbonyl group, elimination is accomplished with formic acid or trifluoroacetic acid; where the protecting group is an orthonitrophenylsulphenyl group, elimination is accomplished with acetic acid or hydrochloric acid; and where the protecting group is a chloroacetyl group, elimination is accomplished with 3-nitropyridine-2-thione [reported by K. Undheim et al: Journal of the Chemical Society, Perkin Transactions, Part I, page 829 (1973)].

In a preferred embodiment, the protecting group is

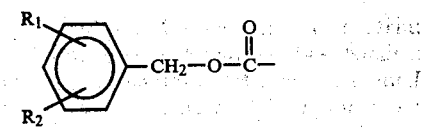

(wherein $R_1$ and $R_2$ have the same significance as defined above) and elimination is carried out by hydrogenolysis in the presence of a metal catalyst selected from palladium, platinum, rhodium and Raney nickel, preferably, palladium catalyst on a carrier of active carbon in at least one solvent selected from the group consisting of tetrahydrofuran, dimethylacetamide, dimethylformamide lower alcohols, dioxane, ethylene glycol dimethyl ether, pyridine and water, preferably, a mixture of water and methanol (1:1); in the presence of a small amount of hydrochloric acid, hydrobromic acid, hydriodic acid or acetic acid, preferably, acetic acid, and at room temperature and at atmospheric pressure. As described above, in the present invention, an acylating agent of the formula:

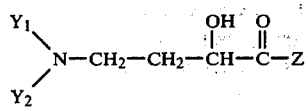

(wherein $Y_1$, $Y_2$ and Z have the same significance as defined above) is used for the preparation of intermediate compounds (IA), (IIA), (IIIA) and (IVA). In accordance with the present invention, it is to be understood that compounds which are functionally equivalent to the above-mentioned acylating agent for introducing an α-hydroxy γ-aminobutyryl group to amino group may also be used as an acylating agent to prepare the intermediate compounds. The introduction of the protecting groups other than $Y_1$ and $Y_2$ to an amino group and the elimination thereof to prepare such acylating agent are described in: M. Bodansky et al: Peptide Synthesis, pages 21-41 (1966) (John Wiley & Sons, Inc., U.S.A.); and A. Kapoor: Journal of Pharmaceutical Sciences, Vol. 59, pages 1-27 (1970).

The thus prepared compounds I, II, III and IV, either prepared from isolated and purified intermediate compounds, IA, IIA, IIIA and IVA, respectively, or from a mixture of compounds IA, IIA, IIIA and IVA, are isolated and purified from the reaction mixture in a known manner. For example, the compounds are isolated and purified by column chromatography using an adsorbent such as ion exchange resins, silica gel, alumina, cellulose, Sephadex, etc., and thin layer chromatography using silica gel, alumina, cellulose, etc.

In the present invention, compounds (I), (II), (III) and (IV) may be in L-, D- or DL-form but, most preferably, the compounds are in L-form.

If desired, compounds I, II, III and IV prepared in accordance with the above may be converted to pharmaceutically acceptable, non-toxic acid addition salts (mono-, di-, tri-, tetra or penta salts) according to conventional methods. In the present invention, non-toxic acids include inorganic acids such as hydrochloric acid, hydrobromic acid, hydriodic acid, sulfuric acid, phosphoric acid, carbonic acid, etc. and organic acids such as acetic acid, fumaric acid, malic acid, citric acid, mandelic acid, tartaric acid, ascorbic acid, etc. The methods for the production of the acid addition salts are well known in the art.

The semi-synthetic derivatives I, II, III and IV of XK-62-2 have an excellent anti-bacterial activity. It is particularly notable that the derivatives have a strong anti-bacterial activity against strains of Escherichia coli having an R factor which shows resistance to known aminoglycoside antibiotics.

Table 1 illustrates the antibacterial spectrum of kanamycin A, gentamicin $C_{1a}$, XK-62-2 and 2'-N-[L-(−)-α-hydroxy-γ-aminobutyryl]XK-62-2 (compound 1), 1-N-[L-(−)-α-hydroxy-γ-aminobutyryl]XK-62-2 (compound II), 1-N-2'-N-bis-[L-(−)-α-hydroxy-γ-aminobutyryl]XK-62-2 (compound III) and 3-N-2'-N-bis[L-(−)-α-hydroxy-γ-aminobutyryl]XK-62-2 (compound IV) against various Gram-negative and Gram-positive bacteria measured by agar-dilution method at pH 8.0.

From a comparison of the minimum inhibitory concentration shown in Table 1, it is apparent that compounds I, II, III and IV have a strong anti-bacterial activity. Characteristically, these compounds show a strong anti-bacterial activity particularly against Escherichia coli KY 8327 and 8348.

Table 1

| | Antibacterial Spectrum (Minimum Inhibitory Concentration, mcg/) | | | | | | |
|---|---|---|---|---|---|---|---|
| | | | | | Compounds | | |
| Strains | Kanamycin A | Gentamicin $C_{1a}$ | XK-62-2 | I | II | III | IV |
| Pseudomonas aeruginosa BMH 1 | 5.2 | 0.13 | 0.52 | 25 | 2.08 | 8.34 | 8.34 |
| Staphylococcus aureus ATCC 6538P | 0.021 | 0.004 | 0.088 | 0.05 | 0.016 | 0.065 | 0.130 |
| Bacillus subtilis No. 10707 | 0.021 | 0.004 | 0.044 | 0.05 | 0.004 | 0.008 | 0.016 |
| Proteus vulgaris ATCC 6897 | 0.16 | 0.033 | 0.033 | 0.39 | 0.065 | 0.521 | 0.521 |
| Shigella seanei ATCC 9250 | 0.16 | 0.033 | 0.033 | 0.39 | 0.033 | 0.260 | 0.260 |
| Salmanella typhosa ATCC 9992 | 0.088 | 0.016 | 0.008 | 0.20 | 0.008 | 0.065 | 0.130 |
| Krobsiella pneumoniae ATCC 10081 | 0.042 | 0.016 | 0.004 | 0.10 | 0.008 | 0.065 | 0.065 |
| Escherichia coli ATCC 26 | 0.16 | 0.033 | 0.016 | 0.39 | 0.004 | 0.065 | 0.130 |
| Escherichia coli KY 8327 | 1.04 | 2.00 | 1.04 | 3.10 | 0.016 | 0.065 | 0.260 |
| Escherichia coli KY 8348 | 0.041 | 1.04 | 1.04 | 0.05 | 0.004 | 0.065 | 0.130 |

In the above table, Escherichia coli KY 8327 and KY 8348 respectively product gentamicin adenyltransferase and gentamicin acetyltransferase Type I intracellularly. The former bacterium inactivates kanamycins and gentamicins by adenylation, and the latter inactivates gentamicins by acetylation.

Further, the antibacterial spectrum of 1-N-[L-(−)-α-hydroxy-γ-aminobutyryl]XK-62-2 (compound II) in comarision with kanamycin A, gentamicin complex ($C_1$, $C_{1a}$ and $C_2$) and XK-62-2 measured by agar dilution method at pH 7.2 is shown in Table 2 below.

In administering the compounds or their acid addition salts, parenteral administration is preferred with an effective dose of 1.6-6-mg/kg per day.

The acute toxicity ($LD_{50}$) of 1-N-[L-(−)-α-hydroxy-γ-aminobutyryl]XK-62-2 (compound II) in mice is 250

Table 2

Antibacterial Spectrum of 1-N-[L-(-)-α-hydroxy-γ-aminobutyryl] XK-62-2

| Strains | Minimum Inhibitory Concentration (mcg/ml) | | | |
|---|---|---|---|---|
| | Kanamycin A | Gentamicin complex ($C_1$, $C_{1a}$ and $C_2$) | XK-62-2 | Compound II |
| staphylococcus aureus 209P | 0.2 | <0.05 | 0.1 | 0.1 |
| staphylococcus aureus Smith | 0.2 | <0.05 | <0.05 | 0.1 |
| Bacillus subtillus ATCC 6688 | 0.2 | <0.05 | <0.05 | 0.1 |
| Sarcina lucca ATCC 9341 | 6.25 | 0.2 | 0.4 | 0.4 |
| Escherichia coli T-2 | 1.56 | 0.4 | 0.4 | 0.4 |
| Escherichia coli T-5 | 1.56 | 0.4 | 0.4 | 0.4 |
| Escherichia coli KY 8327[1] | 50 | 12.5 | 12.5 | 0.2 |
| Escherichia coli KY 8321[2] | 100 | 6.25 | 3.12 | 0.2 |
| Escherichia coli KY 8348[3] | 0.78 | 3.12 | 12.5 | 0.1 |
| Escherichia coli KY 8349[4] | >100 | 0.2 | 0.4 | 0.2 |
| Pseudomonas aeruginosa BMH No. 1 | 12.5 | 0.4 | 0.78 | 1.56 |
| Pseudomonas aeruginosa KY 8510[5] | 100 | 3.12 | 1.56 | 3.12 |
| Pseudomonas aeruginosa KY 8511[6] | 100 | 50 | 100 | 3.12 |
| Pseudomonas aeruginosa KY 8512[7] | 12.5 | 0.4 | 0.78 | 0.78 |
| Pseudomonas aeruginosa KY 8516[8] | >100 | 3.12 | 3.12 | 3.12 |
| providencia sp. 164[9] | >100 | 50 | 100 | 12.5 |
| Klebsiella pneumoniae No. 8045 | 0.4 | 0.2 | 0.1 | 0.2 |
| Proteus Mirabilis 1287 | 6.25 | 1.56 | 0.78 | 3.12 |
| Proteus vulgaris 6897 | 3.12 | 0.78 | 0.78 | 3.12 |
| Proteus rettgeri KY 4288 | 0.78 | 0.78 | 0.4 | 0.78 |
| Proteus marganii KY 4298 | 1.56 | 0.78 | 0.4 | 0.78 |

[1] produces gentamicin adenyltransferase
[2] produces gentamicin adenyltransferase and neamycin-kenamycin phosphotransferase type II
[3] produces gentamicin acetyltransferase Type I
[4] produces neamycin-kanamycin phosphotransferase Type I
[5] produces kanamycin acetyltransferase
[6] produces gentamicin acetyltransferase Type I and neamycin-kanamycin phosphotransferase Type I
[7] produces neamycin-kanamycin phosphotransferase Type I
[8] probably produces kanamycin acetyltranferase
[9] produces gentamicin acetyltransferase Type II
The foregoing enzymes are produced intracellularly and, with the enzyme, the bacteria inactivate antibiotics.

From the above Table 2, it is apparent that 1-N-[L-(−)-α-hydroxy-γ-aminobutyryl] XK-62-2 of the present invention has a very strong antibacterial activity against various bacteria having a resistance to at least one of gentamicin antibiotics and XK-62-2, which produces gentamicin adenyltransferase and/or gentamicin acetyltransferase Type I and Type II intracellularly, thereby inactivating gentamicin antibiotics and XK-62-2.

Moreover, through various tests on the protection against infections induced by the strains of the aforementioned resistance bacteria, the compounds of the invention is revealed to maintain α-hydroxy-γ-aminobutyryl group in vivo and to exhibit much higher antibacterial activity than gentamicin antibiotics and XK-62-2.

From the foregoing tables, it is apparent that compounds I, II, III and IV show a remarkably strong antibacterial activity against a variety of Gram-positive bacteria and Gram-negative bacteria including those resistant to aminoglycoside antibiotics. Therefore, they are expected to be effective for the treatment of various infections in humans and in animals induced by such phlogogenous bacteria. For example, the compounds are expected to be effective for the treatment of urinary tract infections and respiratory infections induced by *Staphylococcus aureus, Escherichia coli, Pseudomonas aeruginosa* and strains of the genus *Proteus*.

mg/kg by intravenous injection, while that of XK-62-2 and the gentamicin complex (a mixture of $C_1$, $C_{1a}$ and $C_2$) are 93 mg/kg and 72 mg/kg, respectively.

Practice of certain specific embodiments of the present invention is illustrated by the following representative examples.

EXAMPLE 1

Production of
2′-N-[L-(−)-α-hydroxy-γ-carbobenzoxyaminobutyryl]XK-62-2 (compound IA),
1-N-[L-(−)-α-hydroxy-γ-carbobenzoxyaminobutyryl]XK-62-2 (compound IIA)(,
1-N-2′-N-bis-[L-(−)-α-hydroxy-carbobenzoxyarnobutyryl]XK-62 -2 (compound IIIA) and
3-N-2′-N-bis-[L-(−)-α-hydroxy-γ-carbobenzoxyaminobutyryl] XK-62-2 (compound IVA)

In this example a sample of XK-62-2 (2.778 g, 6.0 mM) is dissolved in 30 ml of aqueous 50% tetrahydrofuran. To the solution is added a solution of N-hydroxysuccinimide ester of L-(−)-α-hydroxy-γ-carbobentoxyaminobutyric acid [Production of this compound from L-(−)-α-hydroxy-γ-aminobutyric acid is described in the Journal of Antibiotics, Vol. XXV, pages 695–708 (1972). Production of L-(−)-α-hydroxy-γ-aminobutyric acid is described in Tetrahedron Letters, pages 2625–2628 (1971)] (2.94 g, 8.4 mM) in 20 ml of tetrahydrofuran with stirring while maintaining the temperature at −5° to 0° C. The addition is complete in one hour and the mixture is allowed to react over-night.

By silica gel thin layer chromatography (Developer: isopropanol: concentrated aqueous ammonia: chloroform - 2:1 1; coloring agent: nirhydrin), the presence of compounds IA (Rf: 0.75), IIA (Rf: 0.81), IIIA (Rf: 0.86) and IVA (Rf: 0.92) and a small amount of unreacted XK-62-2 is confirmed. The reaction mixture is concentrated under reduced pressure to obtain a slightly yellowish residue which is a mixture of compounds IA, IIA, IIIA and IVA.

EXAMPLE 2

Production of 2'-N-[L-(−)-α-hydroxy-γ-aminobutyryl]XK-62-2 (compound I)

In this example, the mixture of compounds IA, IIA, IIIA and IVA obtained in Example 1 above is dissolved in 40 ml of aqueous 50% methanol. To the solution is added 0.3 ml of acetic acid and the mixture is subjected to hydrogenolysis in the presence of 250 mg of 50 active carbon-palladium at room temperature and at atmospheric pressure for 6 hours. By silica gel thin layer chromatography (under the same conditions as in Example 1), the presence of compounds I (Rf: 0.52), II (Rf: 0.40) III (Rf: 0.31) and IV (Rf: 0.45) in addition to a small amount of unreacted XK-62-2 is confirmed. The catalyst is removed by filtration and the filtrate is concentrated under reduced pressure. To the resulting residue is added 15 ml of water to dissolve the residue and the solution is passed through a column (diameter: 2.5 cm) of Amberlite CG - 50 (ammonium form, 150 ml) product of Rohm and Haas Co., U.S.A.). The column is washed with 200 ml of water. Elution is then carried out with 0.2 N aqueous ammonia and the eluate is taken fractionwise in 10 ml portions. As a result, 0.81 g of XK-62-2 is recovered from fractions Nos. 118-124. Elution is then carried out with 0.4 N aqueous ammonia and compound I is eluted out in fraction Nos. 144-174. These fractions are combined and concentrated to dryness under reduced pressure. As the result, 1.42 g of compound I obtained as a colorless product.

Analysis of compound I reveals the following:
Melting point: 135°-140° C. (decomposition at 143° C.) Specific rotation: $[\alpha]_D^{25} = +131.6°$ (C=0.098, water) Infrared absorption spectrum (KBr) (cm$^{-1}$): 3,700-3,100, 2,950, 1,640, 1,535, 1,490, 1,385, 1,340, 1,287, 1,147, 1,110, 1,055, 1,028, 958, 820, 600 (FIG. 1).

Figure 2:
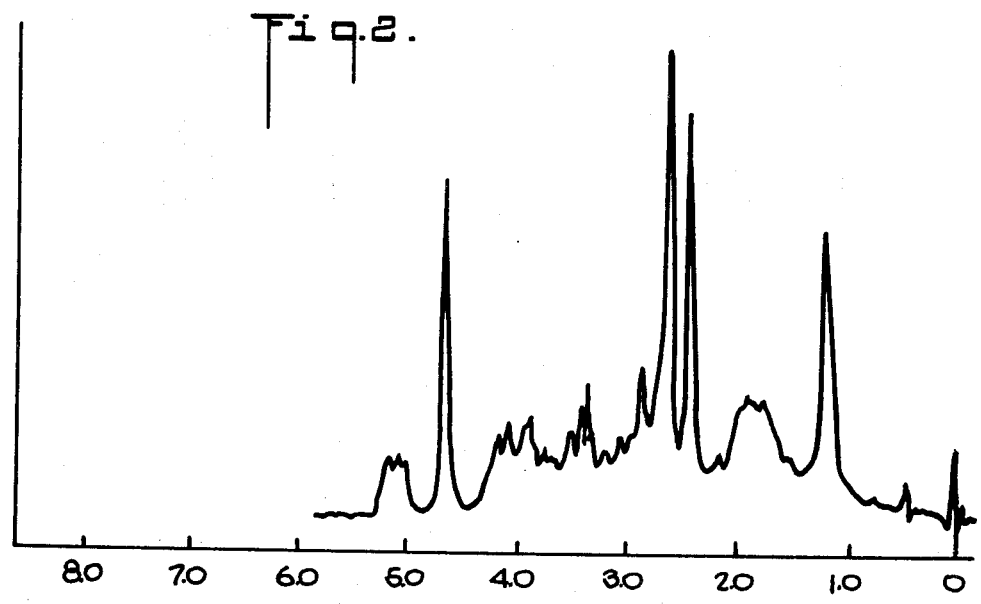
FIG. 2 illustrates the NMR spectrum of 2'-N[L-(—)-α-hydroxy-γ-aminobutyryl] XK-62-2.

Nuclear magnetic resonance (NMR) spectrum (in deuterium oxide) δ in p.p.m. from DSS): 1.18 (3H, singlet), 2.41 (3H, singlet), 2.60 (3H, singlet), 2.83 (2H, singlet), 5.33-4.85 (multiplet overlapping the signal of OH) (FIG. 2).

Elementary analysis: Calculated for $C_{24}H_{48}N_6O_9 \cdot H_3CO_3$ : C=47.91%; H=8.04%; N=13.41% Found: C=47.97%; H=8.27%; N=13.51%

From the foregoing, it is confirmed that compound I has the following structural formula:

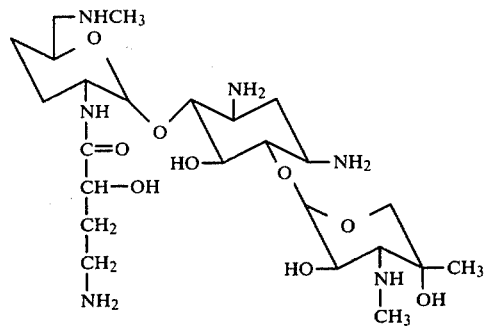

EXAMPLE 3

Production of 1-N-[L-(−)-α-hydroxy-γ-aminobutyryl]XK-62-2 (compound II)

In this example, following the elution of compound I in Example 2, compound II is eluted out in fractions Nos. 225-250. These fractions are combined and concentrated to dryness under reduced pressure to obtain 0.69 g of compound II as a colorless product.

Figure 3:
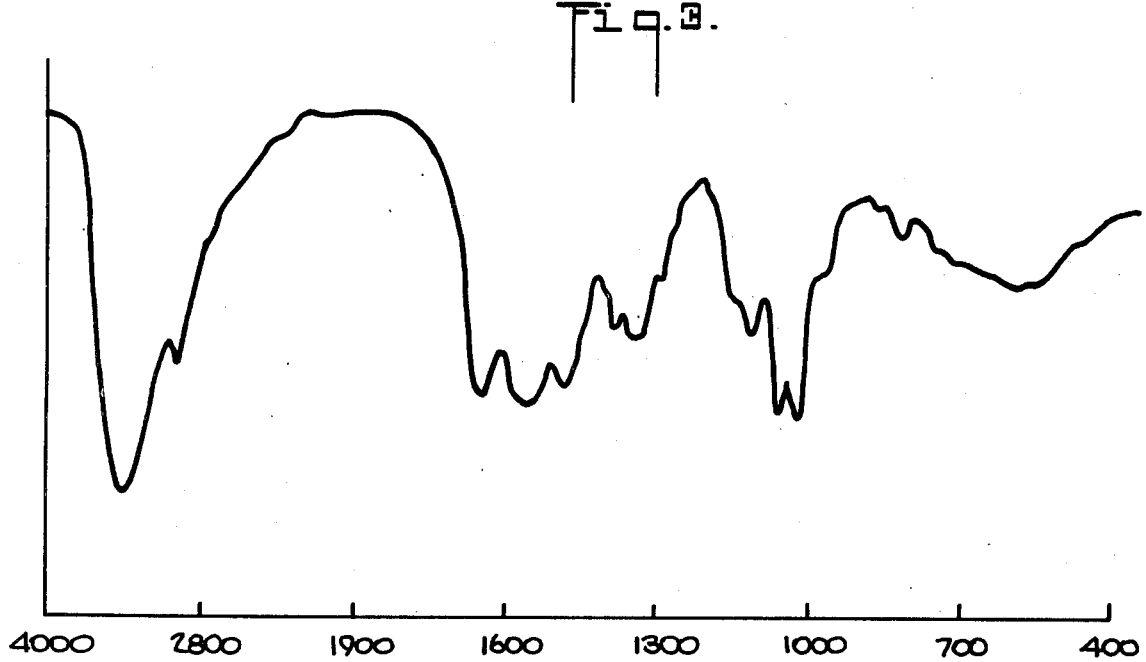
FIG. 3 illustrates the infrared adsorption spectrum of 1-N-[L-(—)-α-hydroxy-γ-aminobutyryl] XK-62-2 (compound II)
Figure 4:
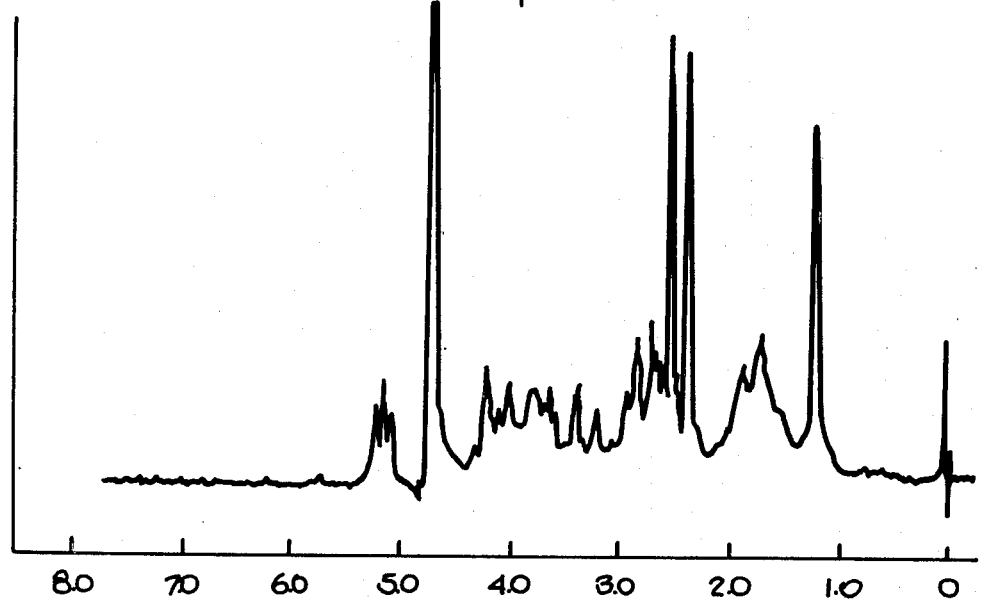
FIG. 4 illustrates the NMR spectrum of 1-N-[L-(—)-α-hydroxy-γ-aminobutyryl] XK-62-2.

Analysis of compound II reveals the following:
Melting point: 120°-124° C.
Specific rotation: $[\alpha]_D^{29} = -59.0°$ (C=0.10, water)
Infrared absorption spectrum (KBr) (cm$^{-1}$): 3,700-3,100, 2,940, 1,640, 1,565, 1,480, 1,385, 1,340, 1,282, 1,111, 1,054, 1,022, 973, 816, 700-600 (FIG. 3).
NMR spectrum (in deuterium oxide) δ (in p.p.m. from DSS): 1.20 (3H, singlet), 2.36 (3H, singlet), 2.52 (3H, singlet), 5.14 (1H, doublet, J=4.0Hz), 5.22 (1H, doublet, J=4.0 Hz) (FIG. 4).

Elementary analysis: Calculated for $C_{24}H_{48}N_6O_9 \cdot 1/2H_2CO_3$: C=49.39%; H=8.29%; N=14.11% Found: C=48.96%; H=8.37%; N=13.95%

Based upon the foregoing it is confirmed that compound II has the following structural formula:

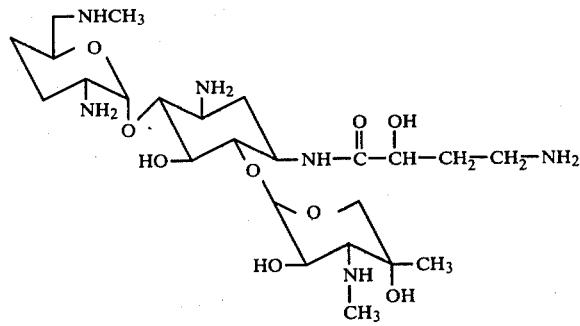

EXAMPLE 4

Production of 3-N-2'-N-bis-[L-(−)-α-hydroxy-δ-aminobutyryl]XK-62-2 (compound IV)

In this example, following elution of compound II in Example 3, compound IV is eluted out in fractions Nos. 273-291. These fractions are combined and concentrated to dryness under reduced pressure to obtain 0.53 g of compound IV as a colorless product.

Analysis of compound IV reveals the following:
Melting Point: 157°-160° C. (decomposition at 167° C.)

Specific rotation: $[\alpha]_D^{14.4} = +56.1°$ (C=0.11, water)

Figure 7:
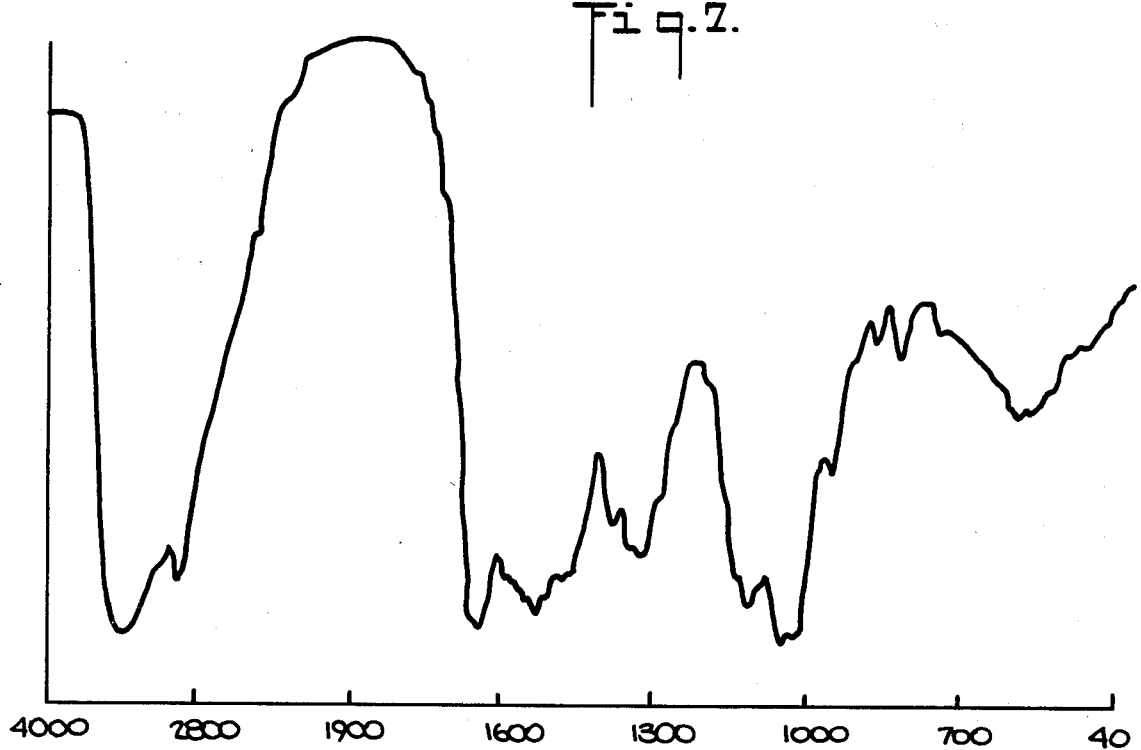
FIG. 7 illustrates the infrared absorption spectrum of 3-N-2'N-bis-[L-(—)-α-hydroxy-γaminobutyryl] XK-62-2 (compound IV)

Infrared absorption spectrum (KBr) (cm$^{-1}$): 3,700–3,000, 2,930, 1,640, 1,525, 1,470, 1,384, 1,320, 1,140, 1,110, 1,050, 1,020, 953, 870, 815, 600 (FIG. 7).

Figure 8:
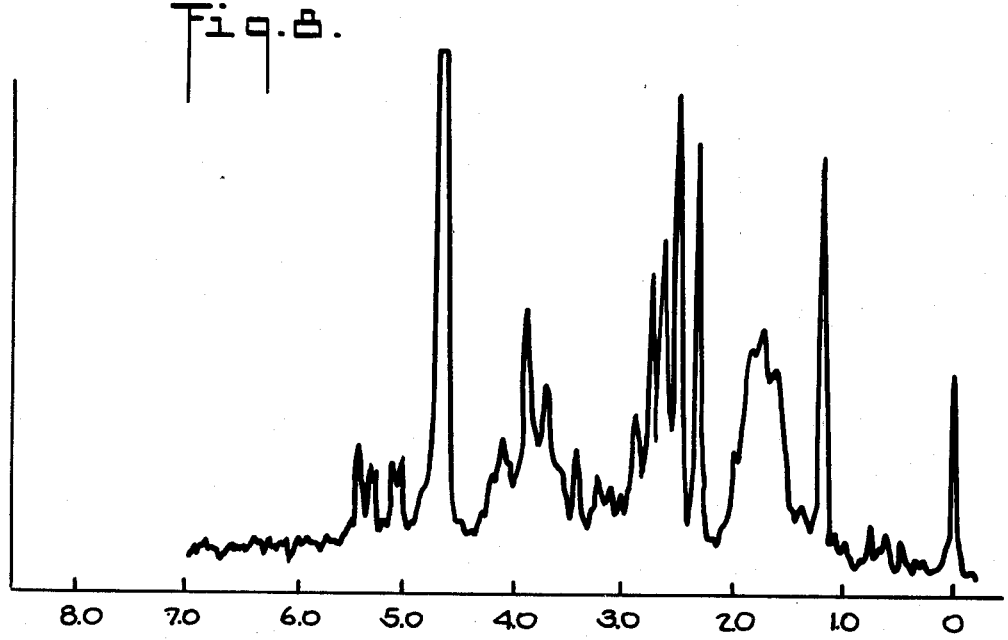
FIG. 8 illustrates the NMR spectrum of 3-N-2'-bis-[L-(—)-α-hydroxy-γ-aminobutyryl] XK-62-2.

NMR spectrum (in deuterium oxide) $\delta$ (in p.p.m. from DSS): 1.22 (3H, singlet), 2.36 (3R, singlet), 2.54 (3H, singlet), 5.12 (1H, doublet, J=4.0 Hz), 5.35 (1H, doublet, J=3.9 Hz) (FIG. 8)

Elementary analysis:

Calculated for $C_{28}H_{55}N_7O_{11} \cdot 3H_2CO_3 \cdot H_2O$: C=42.81%; H=7.52%; N=11.28% Found: C=42.79%; H=7.30%; N=11.20%

From the foregoing, it is confirmed that compound IV has the following structural formula:

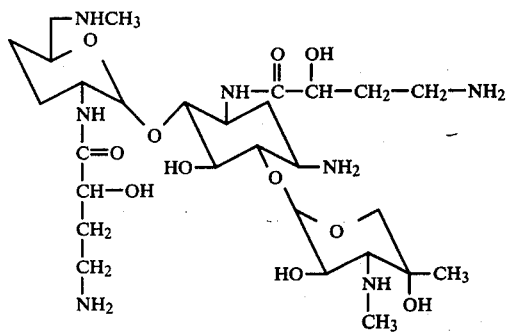

EXAMPLE 5

Production of 1-N-2'-N-bis-[L-(—)-α-hydroxy-δ-aminobutyryl]XK-62-2 (compound III)

In this example, following the elution of compound IV in Example 4, compound III is eluted out in fractions Nos. 315–341. These fractions are combined and concentrated to dryness under reduced pressure to obtain 0.72 g of compound III as a colorless product.

Analysis of compound III reveals the following:

Melting point: 152°–156° C. (decomposition at 160° C.)

Specific rotation: $[\alpha]_D^{25} = +91.7°$(C=0.11, water)

Figure 5:
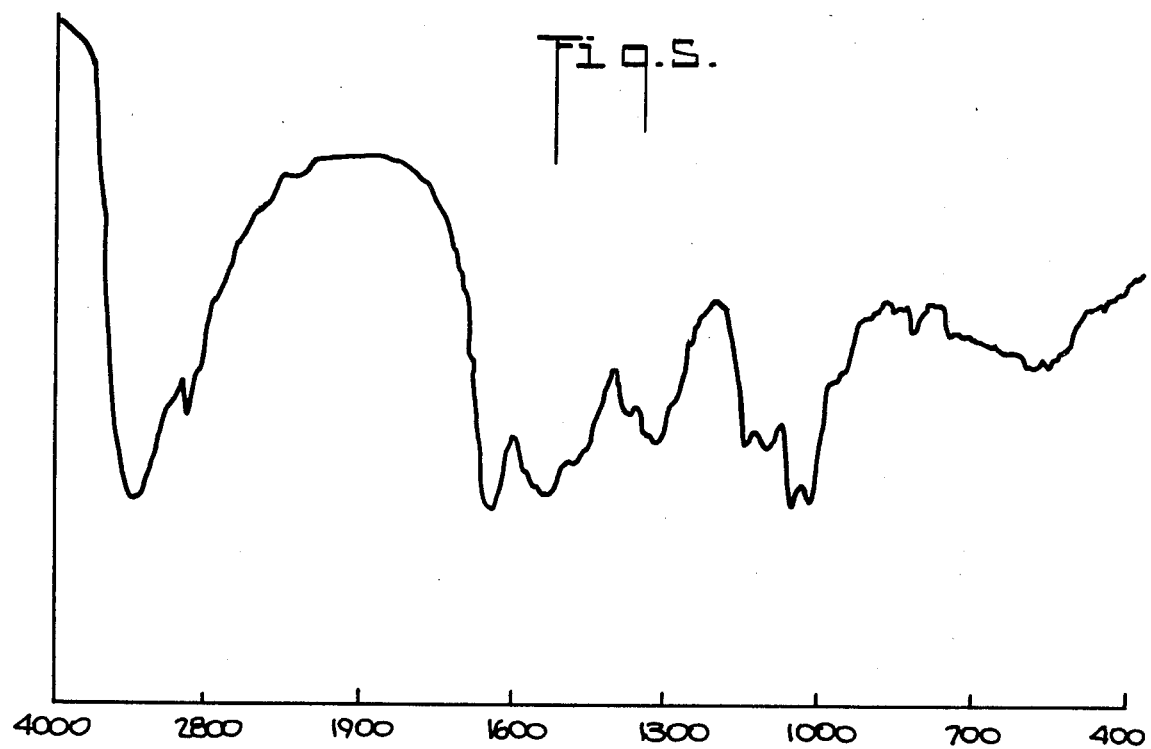
FIG. 5 illustrates the infrared absorption spectrum of 1N-2'-bis-[L-(—)-α-hydroxy-γ-aminobutyry] XK-62-2 (compound III)
Figure 6:
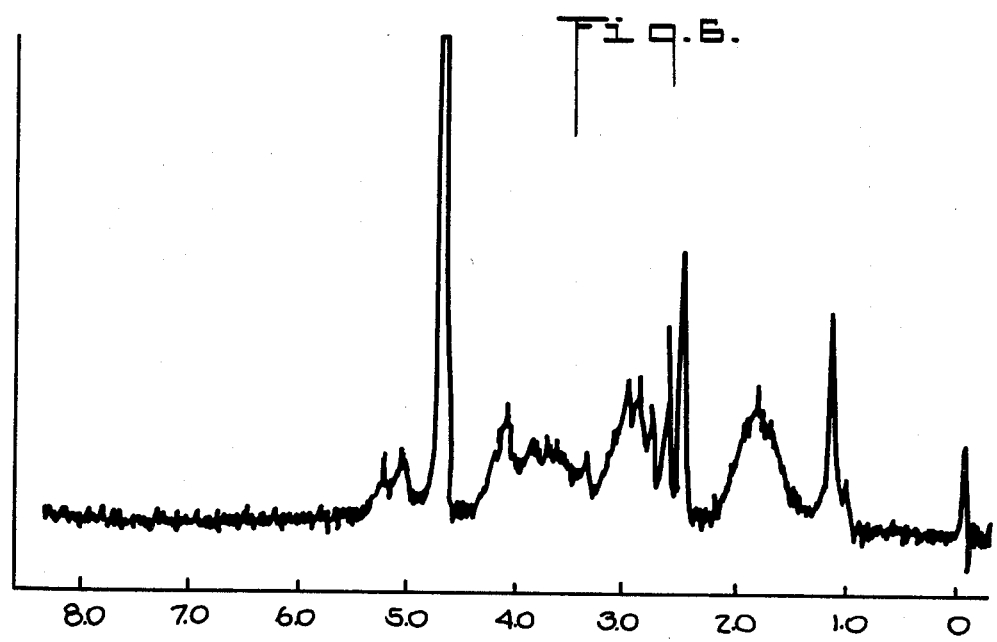
FIG. 6 illustrates the NMR spectrum of 1-N-2'-N-bis-[L-(—)-α-hydroxy-γaminobutyryl] XK-62-2.

Infrared absorption spectrum (KBr) (cm$^{-1}$): 3,700–3,000, 2,960, 1,650, 1,540, 1,490, 1,387, 1,330, 1,150, 1,115, 1,060, 1,023, 960, 820, 600 (FIG. 5) NMR spectrum (in deuterium oxide) $\delta$ in p.p.m. from DSS): 1.22 (3H, singlet), 2.57 (3H, singlet), 2.73 (3H, singlet), 5.40–5.10 (multiplet overlapping the signal of OH) (FIG. 6)

Elementary analysis:

Calculated for $C_{28}H_{55}N_7O_{11} \cdot 2H_2CO_3 \cdot H_2O$: C=44.61%; H=7.56%; N=12.14% Found: C=44.86%; H=7.29%; N=12.31%

From the foregoing, it is confirmed that compound III has the following structural formula:

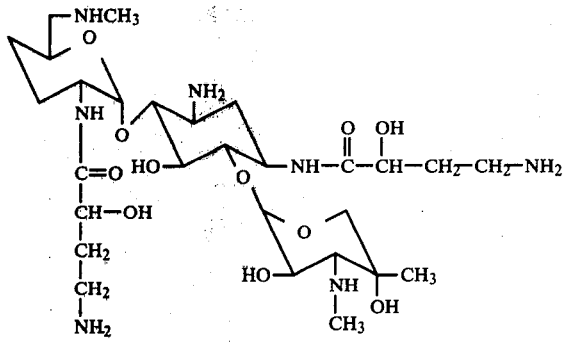

EXAMPLE 6

Production of the monosulfates of compounds I, II, III and IV

In this example, 1 mol of 2'-N-[L-(—)-α-hydroxy-δ-aminobutyryl] XK-62-2 (compound I) is dissolved in 2 L of water. To the solution is added a solution of 1 mol of sulfuric acid in 500 ml of water under cooling conditions. After 30 minutes, cold ethanol is added to the solution to form a precipitate, until the precipitation is complete. The precipitate is separated by filtration to obtain the desired monosulfate of compound I.

The monosulfates of compounds II, III and IV are prepared in the same manner.

What is claimed is:

1. A compound having the formula

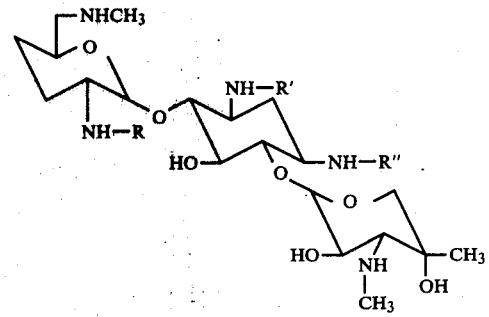

wherein R' is hydrogen and one of R and R" is hydrogen and the other is α-hydroxy-γ-aminobutyryl; or a nontoxic pharmaceutically acceptable acid addition salt thereof.

2. The compound of claim 1 wherein R" is α-hydroxy-γ-aminobutyryl and R' and R" are hydrogen.

3. The compound of claim 1 wherein R" is α-hydroxy-γ-aminobutyryl and R and R' are hydrogen.

4. The monosulfate salt of the compound of claim 2.

5. The monosulfate salt of the compound of claim 3.